(12) United States Patent
Kerr et al.

(10) Patent No.: US 6,780,622 B2
(45) Date of Patent: Aug. 24, 2004

(54) DITERPENE CYCLASE AND METHODS OF USE

(75) Inventors: Russell Kerr, Boca Raton, FL (US); Amber Kohl, Boynton Beach, FL (US)

(73) Assignee: Florida Atlantic University, Boca Raton, FL (US)

( * ) Notice: Subject to any disclaimer, the term of this patent is extended or adjusted under 35 U.S.C. 154(b) by 34 days.

(21) Appl. No.: 10/351,766

(22) Filed: Jan. 27, 2003

(65) Prior Publication Data

US 2003/0153052 A1 Aug. 14, 2003

Related U.S. Application Data

(60) Provisional application No. 60/351,984, filed on Jan. 25, 2002.

(51) Int. Cl.[7] .............................. C12N 9/00; C12Q 1/00; C07K 17/00
(52) U.S. Cl. ............................ 435/183; 435/4; 530/350
(58) Field of Search ...................... 435/4, 183; 530/350

(56) References Cited

U.S. PATENT DOCUMENTS

| | | | |
|---|---|---|---|
| 6,046,041 A | 4/2000 | Kerr | |
| 2002/0091093 A1 | 7/2002 | Jacobs et al. | |
| 2003/0104007 A1 | 6/2003 | Jacobs et al. | |

OTHER PUBLICATIONS

Witkowski et al. , Biochemistry 38:11643–11650, 1999.*
Bork ,Genome Research, 10:398–400, 2000.*
Broun et al. , Science 282:1315–1317, 1998.*
Seffernick et al. , J. Bacteriol. 183(8):2405–2410, 2001.*
Van de Loo et al. , Proc. Natl. Acad. Sci. 92:6743–6747, 1995.*
Coleman A. and R. Kerr, "Radioactivity–Guided Isolation and Characterization of the Bicyclic Pseudopterosin Diterpene Cyclase Product from Pseudopterogorgia elisabethae," Tetrahedron, 56: 9569–9574, 2000.
Bonk et al., "Chloroplast import of four cartenoid biosynthetic enzymes in vitro reveals differential fates prior to membrane binding and oligomeric assembly," Eur. J. Biochem, 247: 942–950, 1997.
Ata et al., "Identification of anti–inflammatory diterpenses from the marine gorgonian Pseudopterogorgia elisabethae," Tetrahedron, 50: 4215–4222, 2003.

Mu et al., "Coupling of Isoprenoid Triflates with Organoboron Nucleophiles: Synthesis and Biological Evaluation of Geranylgeranyl Diphosphate Analogues," Bioorganic & Medicinal Chemistry, 10: 1207–1219, 2002.
Quellhorst et al., "Modification of Rab5 with a photoactivatable analog of geranylgeranyl diphosphate," Journal of Biological Chemistry, 44: 40727–40733, 2001 Abstract.
Shao et al., "Sterospecific Synthesis and Biological Evaluation of Farnesyl Diphosphate Isomers," Organic Letters, 1: 627–630, 1999.
Micali et al., "Protein Farnesyltransferase Isoprenoid Substrate Discrimination Is Dependent on Isoprene Double Bonds and Branched Methyl Groups," Biochemistry, 40: 12254–12265, 2001.
Chehade et al., "Photoaffinity Analogues of Farnesyl Pyrophosphate Transferable by Protein Farnesyl Transferase," J. Am. Chem. Soc., 124: 8206–8219, 2002.
Thoma et al., "Phosphoisoprenoid Binding Specificity of Geranylgeranyltransferase Type II," Biochemistry, 39: 12043–12052, 2000.
Garrett, J., "Benzocyclobutene Via Catalytic Dehydrogenation," Tetrahedron Letters, 3: 191–194, 1969.
Neumann, R., "Aromatization of Hydrocarbons by Oxidative Dehydrogenation Catalyzed by the Mixed Addenda Heteropoly Acid $H_5PMo_{10}V_2O_{40}$," American Society, 1989.
Bernini et al., "Aromatic ring hydroxylation of flavanones by dimethyldioxirance," Bioorganic & Medicinal Chemistry Letters, 8: 2945–2948, 1998.
Matsumoto et al., "Synthesis of Anti–Rheumatic Agent Epoxyquinomicin B," Bioorganic & Medicinal Chemistry Letters, 8: 2945–2948, 1998.
Bozell, J. and J. Hoberg, "Catalytic Oxidation of Para–Substituted Phenols with Nitrogen Dioxide and Oxygen," Tetrahedron Letters, 39: 2261–2264, 1998.

* cited by examiner

Primary Examiner—Rebecca Prouty
Assistant Examiner—Delia M. Ramirez
(74) Attorney, Agent, or Firm—Akerman Senterfitt; Stanley A. Kim

(57) ABSTRACT

An enzyme having diterpene cyclase activity has been purified from P. elisabethae using a series of chromatography steps. The purified enzyme has an apparent molecular weight of about 47 kilodaltons and an isoelectric point of about 5.1. The purifed enzyme catalyzed the cyclization of geranyl geranyl diphosphate to elisabethatriene.

8 Claims, 4 Drawing Sheets

Peptide sequence AK #01 =

Gly-Gln-Leu-Asp-Met-His-Asp-Pro-Ile (SEQ ID NO:1)

Peptide sequence AK #02 =

Gly-Tyr-Pro-Asn-Phe-Pro-Ser-Ile-Ser-Glu-Met-Lys (SEQ ID NO:2)

Peptide sequence AK #03 =

Arg-Asp-Glu-Tyr-Gly-Asn-X-Val-Val-Glu-Thr-Phe-Val-Glu-Asn-Leu (SEQ ID NO:3)

Peptide sequence AK #04 =

Gly-Leu-Leu-Asp-Ala-Leu-Gln-Gly-Ile-Val-Asp-Gly-Arg-Asp (SEQ ID NO:4)

FIG. 4

SEQUENCE LISTING

```
<160> NUMBER OF SEQ ID NOS: 4

<210> SEQ ID NO 1
<211> LENGTH: 9
<212> TYPE: PRT
<213> ORGANISM: Pseudopterogorgia elisabethae

<400> SEQUENCE: 1

Gly Gln Leu Asp Met His Asp Pro Ile
1               5

<210> SEQ ID NO 2
<211> LENGTH: 12
<212> TYPE: PRT
<213> ORGANISM: Pseudopterogorgia elisabethae

<400> SEQUENCE: 2

Gly Tyr Pro Asn Phe Pro Ser Ile Ser Glu Met Lys
1               5                   10

<210> SEQ ID NO 3
<211> LENGTH: 16
<212> TYPE: PRT
<213> ORGANISM: Pseudopterogorgia elisabethae
<220> FEATURE:
<221> NAME/KEY: MISC_FEATURE
<222> LOCATION: (7)..(7)
<223> OTHER INFORMATION: X denotes an ambiguous residue

<400> SEQUENCE: 3
```

-continued

```
Arg Asp Glu Tyr Gly Asn Xaa Val Val Glu Thr Phe Val Glu Asn Leu
1               5                   10                  15

<210> SEQ ID NO 4
<211> LENGTH: 14
<212> TYPE: PRT
<213> ORGANISM: Pseudopterogorgia elisabethae

<400> SEQUENCE: 4

Gly Leu Leu Asp Ala Leu Gln Gly Ile Val Asp Gly Arg Asp
1               5                   10
```

DITERPENE CYCLASE AND METHODS OF USE

CROSS REFERENCE TO RELATED APPLICATION

Figure 1:
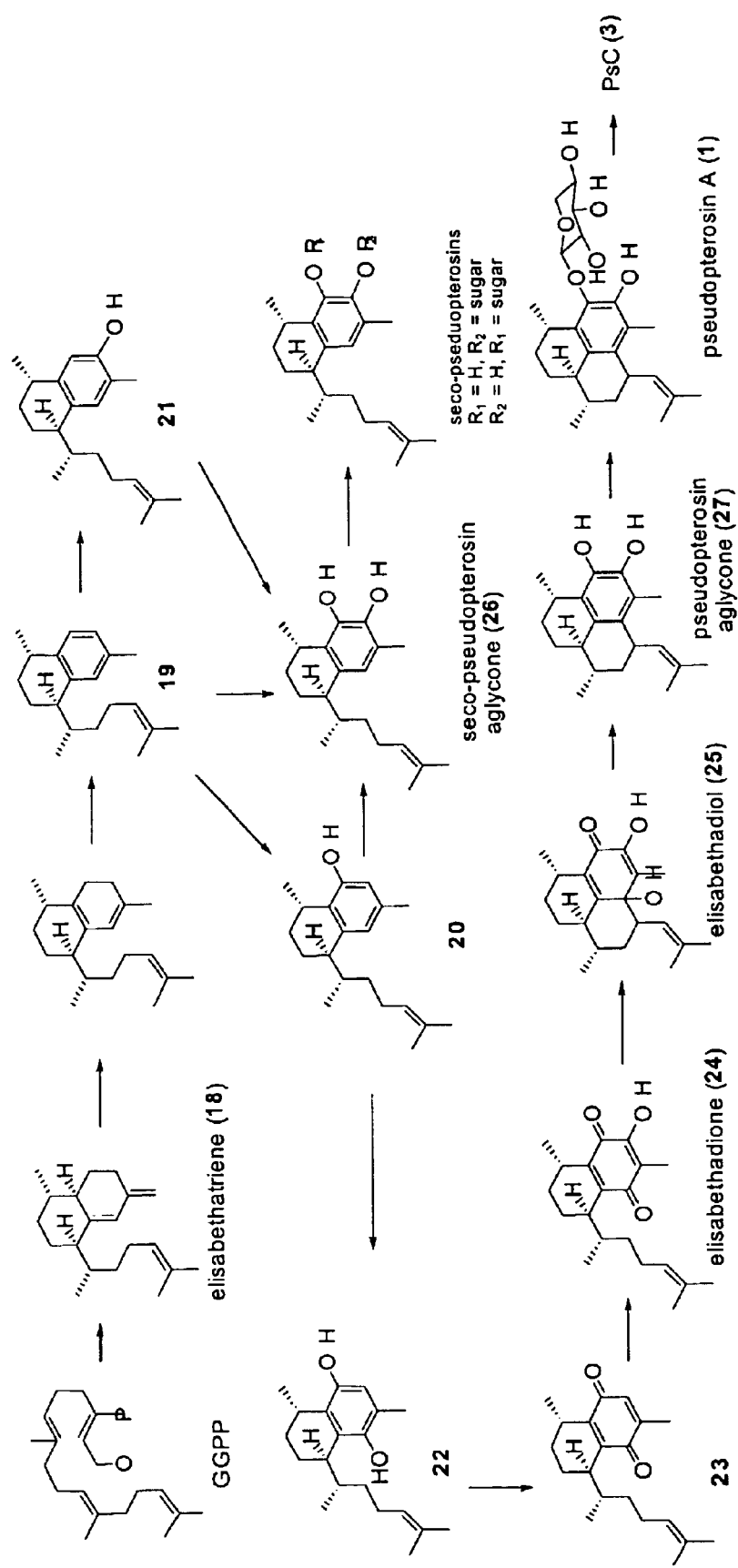

The present application claims the priority of U.S. provisional application No. 60/351,984 filed Jan. 25, 2002.

STATEMENT AS TO FEDERALLY-SPONSORED RESEARCH

Not applicable.

FIELD OF THE INVENTION

The invention relates generally to the fields of biochemistry, enzymology, and marine biology. More particularly, the invention relates to a purified enzyme useful for producing pseudopterosins.

BACKGROUND

*Pseudopterogorgia elisabethae*, a purple frilly seafan, is a gorgonian commonly found in the shallow-water reefs of the tropical Atlantic including regions of the Caribbean. *P. elisabethae* is of particular commercial importance as it has been found to contain numerous biologically active small molecule compounds. Among these, pseudopterosins (also known as terpenes, e.g., diterpenes) have been shown to exhibit anti-inflammatory and analgesic properties, and are currently being used as topical agents in skin care products. In the biosynthetic pathway shown in FIG. 1, pseudopterosin/seco-pseudopterosins are generated from geranyl geranyl diphosphate (GGPP). A key step in this pathway is the cyclization of GGPP to elisabethatriene (compound 18). From elisabethatriene, the intermediate compounds 19–27 and pseudopterosin A are made. The identification of enzymes responsible for catalyzing key steps in this pathway, however, has been elusive. Identification of such an enzyme would facilitate the development of a chemoenzymatic method for the production of marine diterpenes.

SUMMARY

The invention relates to the purification and partial sequencing of an elisabethatriene cyclase from *P. elisabethae*. This cyclase is useful for converting GGPP to elisabethatriene, a step involved in the production of seco-psuedopterosins, pseudotopterosins, and related molecules. The purified enzyme is useful for synthesizing the foregoing molecules. In addition, the purified cyclase should be useful for making other diterpenes. The methods disclosed herein might also be used to produce eleutherobin, an antimitotic agent isolated from the soft coral *Erythropodium caribaeorum*.

Accordingly, the invention features a purified elisabethatriene cyclase such as a purified protein isolatable from a *Pseudopterogorgia elisabethae* coral sample having an apparent molecular weight of about 47,000 Da; an isoelectric point of about 5.1; and the ability to cyclize geranyl geranyl diphosphate. The purified protein can be one that includes the amino acid sequence of SEQ ID NO:1, SEQ ID NO:2, SEQ ID NO:3 and/or SEQ ID NO:4. Fragments of the foregoing that are capable of catalyzing the formation of elisabethatriene from geranyl geranyl diphosphate are also featured in the invention.

In another aspect the invention features a method of purifying an elisabethatriene cyclase from a *Pseudopterogorgia elisabethae* sample. This method includes the steps of: (A) preparing a cell free extract from a *Pseudopterogorgia elisabethae* sample; (B) separating the cell free extract into at least two fractions, one that exhibits elisabethatriene cyclase activity and one that does not; and (C) collecting the fraction that exhibits elisabethatriene cyclase activity. The step (A) of preparing a cell free extract from the *Pseudopterogorgia elisabethae* sample can be performed by flash freezing the *Pseudopterogorgia elisabethae* sample using liquid nitrogen; homogenizing the frozen sample with a buffer and liquid nitrogen; separating the homogenized sample into a cellular portion and a non-cellular portion; and collecting the non-cellular portion. The step (B) of separating the cell free extract can be performed by subjecting the cell free extract to one or more chromatographic separation steps such as DEAE ion exchange chromatography, phenyl sepharose chromatography, hydroxyapatite chromatography, and/or ion exchange chromatography with 2-Propen-1-aminium, N,N,-dimethyl-N-2-propenyl-, chloride, polymer with 1,4-bis(1-oxo-2-propenyl) piperazine and 2-methyl-2-propenamide.

The invention also provides a method for cyclizing geranyl geranyl diphosphate, e.g., to make elisabethatriene. This method is performed by contacting geranyl geranyl diphosphate with a purified elisabethatriene cyclase under reaction conditions that result in the production of elisabethatriene. The elisabethatriene thus formed can be used as a substrate to produce other molecules involved in pseudopterosin synthesis. For example, elisabethatriene can be reacted to produce elisabethadione which can be reacted to produce elisabethadiol. The latter can be reacted to produce pseudopterosin agylcone which can be reacted to produce pseudopterosin A.

Unless otherwise defined, all technical terms used herein have the same meaning as commonly understood by one of ordinary skill in the art to which this invention belongs. Definitions of molecular biology terms can be found, for example, in Rieger et al., Glossary of Genetics: Classical and Molecular, 5th edition, Springer-Verlag: New York, 1991; and Lewin, Genes V, Oxford University Press: New York, 1994. Definitions of organic chemistry and enzymology can be found, for example, in R. B. Silverman et al., The Organic Chemistry of Enzyme-Catalyzed Reactions, Academic Press: San Diego, Calif., 2000; and R. T. Morrisson et al., Organic Chemistry, 6th edition, Addison-Wesley Publishing Co.: Boston, Mass., 1992.

As used herein, the terms "protein" and "polypeptide" are used synonymously to mean any peptide-linked chain of amino acids, regardless of length or post-translational modification, e.g., glycosylation or phosphorylation. A "purified" polypeptide is one that has been substantially separated or isolated away from other polypeptides in a cell, organism, or mixture in which the polypeptide occurs (e.g., 30, 40, 50, 60, 70, 80, 90, 95, 96, 97, 98, 99, 100% free of contaminants).

A "purified elisabethatriene cyclase" is a purified protein isolatable from *P. elisabethae* that has the ability to cyclize GGPP. The phrase includes the purified native form of elisabethatriene cyclase isolatable from *P. elisabethae* and having an apparent molecular weight of about 47,000 Da and an isoelectric point of about 5.1. It also includes naturally occurring and non-naturally occurring proteins having a similar structure (e.g., sharing 65, 70, 75, 80, 85, 90, 95, 97, 98, 99% or more sequence identity) and enzymatic activity, e.g., allelic variants of a native elisabethatriene cyclase, mutants of a native elisabethatriene cyclase, and forms of the enzyme produced by recombinant DNA technology or chemical synthesis.

A "fragment" of an elisabethatriene cyclase polypeptide is a portion of an elisabethatriene cyclase polypeptide that is less than full-length (e.g., a polypeptide consisting of 5, 10, 15, 20, 30, 40, 50, 75, 100 or more amino acids of native elisabethatriene cyclase polypeptide), and preferably retains at least one functional activity of native elisabethatriene cyclase polypeptide (e.g., the ability to cyclize a GGPP substrate).

The term "antibody" includes polyclonal and monoclonal antibodies as well as antibody fragments or portions of immunolglobulin molecules that can specifically bind the same antigen as the intact antibody molecule.

As used herein, "bind," "binds," or "interacts with" means that one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ liters/mole for that second molecule.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 1 is a schematic overview of pseudopterosin/seco-pseudopterosin biosynthesis pathways.

FIG. 2 is sodium dodecyl sulfate polyacrylamide gel electrophoresis (SDS-PAGE) analysis of chromatography fractions. Lane: 1) Low Molecular Weight Standard, 2) Cell-Free Extract, 3) Ion Exchange, 4) Dye Ligand, 5) Hydroxyapatite, 6) Purified Gel Slice.

FIG. 3 is a schematic overview of the chemical transformation of elisabethatriene to elisabethadione.

FIG. 4 is a set of amino acid sequences (SEQ ID NOs:1–4) corresponding to elisabethatriene cyclase peptide fragments purified from *P. elisabethae.*

DETAILED DESCRIPTION

Elisabethatriene cyclase, an enzyme having diterpene cyclase activity, was purified from *P. elisabethae* by separating a cell free extract of the coral using a series of chromatographic steps. Biochemical characterization of the purified protein indicated that it had an apparent molecular weight of about 47,000 Da and an isoelectric point of about 5.1. The enzyme was partially sequenced. The purified enzyme retained its diterpene cyclase activity as evidenced by its ability to cyclize GGDP. This purified enzyme is thus useful in methods of making elisabethatriene from a GGDP substrate and in methods for producing diterpenes such as pseudopterosins, seco-pseudopterosins, and structurally related molecules.

The below described preferred embodiments illustrate adaptations of these compositions and methods. Nonetheless, from the description of these embodiments, other aspects of the invention can be made and/or practiced based on the description provided below.

Biological Methods

Methods involving conventional biological techniques are described herein. Such techniques are generally known in the art and are described in detail in methodology treatises such as Molecular Cloning, 3rd Edition, Sambrook and Russell, Cold Spring Harbor Press, 2001; and Current Protocols in Molecular Biology, ed. Ausubel et al., Greene Publishing and Wiley-Interscience, New York, 1992 (with periodic updates). Methods in enzymology are discussed in Guide to Protein Purification: Methods in Enzymology, Vol. 182, ed. M. P. Deutscher, Academic Press: San Diego, Calif., 1990.

Elisabethatriene Cyclase

The present invention provides a purified elisabethatriene cyclase polypeptide. A preferred form of the elisabethatriene cyclase for use in the invention is the native form of the enzyme that can be isolated from *P. elisabethae* according to the methods described below. Biochemical characterization of the native form of elisabethatriene cyclase indicated that it has an apparent molecular weight of about 47 kilodaltons and an isoelectric point of about 5.1. Partial amino acid sequencing indicated that this enzyme includes peptides having the sequences described herein as SEQ ID NOs:1–4. In addition to the native form, other variant forms of this enzyme are included within the invention. Variants include fragments, analogs and derivatives of native elisabethatriene cyclase and may be made according to methods commonly known in the art. For example, such variants include a polypeptide encoded by a naturally occurring allelic variant of native elisabethatriene cyclase-encoding nucleotide sequence, a polypeptide encoded by a homolog of native elisabethatriene cyclase-encoding nucleotide sequence, and a polypeptide encoded by a non-naturally occurring variant of native elisabethatriene cyclase-encoding nucleotide sequence.

Elisabethatriene cyclase polypeptide variants have a peptide sequence that differs from native elisabethatriene cyclase polypeptide in one or more amino acids. The peptide sequence of such variants can feature a deletion, addition, or substitution of one or more amino acids of a native elisabethatriene cyclase polypeptide. Amino acid insertions are preferably of about 1 to 4 contiguous amino acids, and deletions are preferably of about 1 to 10 contiguous amino acids, and deletions are preferably of about 1 to 10 contiguous amino acids. In some applications, variant elisabethatriene cyclase polypeptides substantially maintain a native elisabethatriene cyclase polypeptide functional activity (e.g., cyclase activity). For other applications, variant elisabethatriene cyclase polypeptides lack or feature a significant reduction in a elisabethatriene cyclase polypeptide functional activity. Where it is desired to retain a functional activity of native elisabethatriene cylcase, preferred elisabethatriene cyclase variants can be made by expressing nucleic acid molecules within the invention that feature silent or conservative changes. Variant elisabethatriene cyclase polypeptides with substantial changes in functional activity can be made by expressing nucleic acid molecules that feature less than conservative changes.

Elisabethatriene cyclase polypeptide fragments corresponding to one or more particular motifs and/or domains or to arbitrary sizes, for example, at least 5, 10, 25, 50, 75, 100, 125, 150, 175, 200, 250, 300, 350 and 400 amino acids in length are within the scope of the present invention. Isolated peptidyl portions of elisabethatriene cylcase proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an elisabethatriene cyclase polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of native elisabethatriene cyclase.

Another aspect of the present invention concerns recombinant forms of the elisabethatriene cyclase polypeptides. Recombinant polypeptides preferred by the present invention, in addition to native elisabethatriene cyclase, are encoded by a nucleic acid that has at least 85% sequence identity (e.g., 85, 86, 87, 88, 89, 90, 91, 92, 93, 94, 95, 96, 97, 98, 99, 100%) with a nucleic acid encoding native elisabethatriene cyclase. In a preferred embodiment, an elisabethatriene cyclase of the present invention is a coral elisabethatriene cyclase. In a particularly preferred embodiment, an elisabethatriene cyclase has one or more functional activities of native elisabethatriene cyclase.

Elisabethatriene cyclase variants can be generated through various techniques known in the art. For example, elisabethatriene cyclase variants can be made by mutagenesis, such as by introducing discrete point mutation (s), or by truncation. Mutation can give rise to an elisabethatriene cyclase variant having substantially the same, or merely a subset of the biological activity of native elisabethatriene cyclase. Other variants of elisabethatriene cyclase that can be generated include those that are resistant to proteolytic cleavage. Whether a change in the amino acid sequence of a peptide results in an elisabethatriene cyclase variant having one or more functional activities of native elisabethatriene cyclase can be readily determined by testing the variant for a native elisabethatriene cyclase functional activity in one or more of the assays described herein.

Purification of Elisabethatriene Cyclase

Elisabethatriene cyclase can be purified from a coral such as *P. elisabethae* by adapting a variety of known protein purification techniques. In the example described below, *P. elisabethae* coral samples were flash frozen using liquid nitrogen and then stored at −80° C. prior to use. Rapid freezing appeared to be important in maintaining the activity of the enzyme. The frozen samples were homogenized and centrifuged to remove insoluble debris. The resultant supernatant or cell free extract (CFE) was subjected to chromatographic separation. Those fractions containing diterpene cyclase activity were the fractions that contained the purified enzyme.

Diterpene cyclase activity can be assessed using any suitable substrate cyclization assay. For example, test samples/fractions can be incubated with radiolabeled (e.g., $^3$H) substrate (e.g., 1 $\mu$Ci GGPP) at a temperature of about 27° C. for approximately 1–4 hours. The amount of GGPP cyclized to elisabethatriene can then be determined.

Chromatographic separation of a CFE can be performed using a variety of known techniques in chromatography. For example, proteins in CFE can be separated according to molecular weight (e.g., using size exclusion chromatography) and/or charge (e.g., using ion exchange chromatography). In the method described below, a series of chromatographic steps including DEAE ion-exchange chromatography, phenyl sepharose chromatography, hydroxyapatite chromatography, and UNO™ (Bio-Rad, Hercules, Calif.) chromatography was employed. Other techniques may also be used to purify elisabethatriene cyclase. For example, in addition to conventional column chromatography, high-performance liquid chromatography (HPLC) and preparative electrophoresis might be used.

The isolation and purification methods described herein can be applied to the isolation and purification of cyclases from organisms other than *P. elisabethae* (e.g., *Erythropodium caribaeorum*). For example, a purified *E. caribaeorum* cyclase would be useful for producing eleutherobin, an antimitotic agent isolated from *E. caribaeorum*.

Methods for Cyclizing A Substrate

The invention provides compositions and methods for cyclizing a substrate (e.g., GGPP to elisabethatriene) using a purified elisabethatriene cyclase. A preferred substrate for cyclization is GGPP. Other potential substrates include GGPP analogues including 3-PhGGPP (see Mu et al., Bioorg. Med. Chem. 10:1207–1219, 2002; and Quellhorst et al., J. Biol. Chem. 276:40727–40733, 2001), farnesyl diphosphate (also known as farnesyl pyrophosphate, FPP), isomers of FPP (see Shao et al., Org. Lett. 1:627–630, 1999), FPP analogues (see Micali et al., Biochemistry 40:12254–12265, 2001; and Chehade et al., J. Am. Chem. Soc. 124:8206–8219, 2002), as well as other phosphoisoprenoids (see Thoma et al., Biochemistry 39:12043–12052).

An example of a method for cyclizing GGPP to elisabethatriene includes the steps of providing purified elisabethatriene cyclase and contacting the GGPP substrate with the purified elisabethatriene cyclase under reaction conditions that result in the production of elisabethatriene. Any suitable reaction conditions that result in the production of elisabethatriene may be used. For example, $^3$H-GGPP (1 $\mu$Ci) is incubated with a suitable amount of purified elisabethatriene cyclase at 27° C. for 1–4 hours.

Pseudopterosin Biosynthesis

The invention provides methods for producing diterpenes, also known as pseudopterosins. Such compounds have been isolated from marine corals and many are useful as components in skin care products. Once GGPP has been cyclized to produce elisabethatriene using the methods described herein, purified elisabethatriene can be used in methods to produce pseudopterosins. For example, elisabethatriene can be aromatized using either Pd or a heteropoly acid in high yield (80–85%). The resulting aromatic hydrocarbon could presumably be oxidized and subsequently glycosylated using methods available in the literature to generate a pseudopterosin-like molecule.

Anti-Elisabethatriene Cyclase Antibodies

Elisabethatriene cyclase polypeptides (or immunogenic fragments or analogs thereof) can be used to raise antibodies useful in the invention. Such polypeptides can be produced by recombinant techniques or synthesized as described above. In general, elisabethatriene cyclase polypeptides can be coupled to a carrier protein, such as KLH, as described in Ausubel et al., supra, mixed with an adjuvant, and injected into a host animal. Antibodies produced in that animal can then be purified by peptide antigen affinity chromatography.

In particular, various host animals can be immunized by injection with an elisabethatriene cyclase polypeptide or an antigenic fragment thereof. Commonly employed host animals include rabbits, mice, guinea pigs, and rats. Various adjuvants that can be used to increase the immunological response depend on the host species.

Antibodies within the invention therefore include polyclonal antibodies and, in addition, monoclonal antibodies (mAbs), single chain antibodies, Fab fragments, F(ab')$_2$ fragments, and molecules produced using a Fab expression library. Such antibodies can be of any immunoglobulin class including IgG, IgM, IgE, IgA, IgD and any subclass thereof. A hybridoma producing mAbs of the invention may be cultivated in vitro or in vivo. The ability to produce high titers of mAbs in vivo makes this a particularly useful method of production.

Once produced, polyclonal or monoclonal antibodies can be tested for specific elisabethatriene cyclase recognition by Western blot or immunoprecipitation analysis by standard methods, for example, as described in Ausubel et al., supra. Antibodies that specifically recognize and bind to elisabethatriene cyclase are useful in the invention. For example, such antibodies can be used in an immunoassay to monitor the level of elisabethatriene cyclase produced by a coral (e.g., to determine the amount or subcellular location of elisabethatriene cyclase).

The antibodies of the invention can be used, for example, in the detection of elisabethatriene cyclase in a biological sample. Antibodies also can be used in a screening assay to measure the effect of a candidate compound on expression or localization of elisabethatriene cyclase. Additionally, such antibodies can be used to interfere with the interaction of elisabethatriene cyclase and other molecules that bind elisabethatriene cyclase.

The present invention is further illustrated by the following specific examples. The examples are provided for illustration only and are not to be construed as limiting the scope or content of the invention in any way.

EXAMPLES

Example 1
Isolation and Purification of Elisabethatriene Cyclase

*P. elisabethae* was collected from various sites in the Bahamas as well as in the Florida Keys. The harvested coral was immediately flash frozen in liquid nitrogen and stored at −80° C. A CFE was prepared by homogenizing the flash frozen coral with phosphate buffer (pH 7.7, 5 mM β-mercaptoethanol and 1 mM MgCl$_2$) and liquid nitrogen. The homogenate was centrifuged at low speed to remove insoluble debris and the supernatant used as the CFE.

Enzymatic activity in CFE preparations was typically assessed by incubating $^3$H-GGPP (1 μCi) with 30 mL of CFE at 27° C. for 1–4 hours. All CFE preparations analyzed showed the ability to catalyze the cyclization of GGPP to elisabethatriene. In other studies, CFE was shown to transform elisabethatriene to the pseudopterosins. Adding protease inhibitors in this process did not increase the enzymatic activity of the CFE.

To purify enzymatically active elisabethatriene cyclase, CFE samples were subjected to DEAE ion-exchange chromatography, phenyl sepharose chromatography, hydroxyapatite chromatography, and UNO™ [2-Propen-1-aminium, N,N,-dimethyl-N-2-propenyl-, chloride, polymer with 1,4-bis(1-oxo-2-propenyl)piperazine and 2-methyl-2-propenamide] ion exchange chromatography (Bio-Rad Laboratories, Hercules, Calif.). Active fractions were obtained in all cases. Fractions resulting from these purification techniques were concentrated by ultracentrifugation, and then 0.5–100 μg (brought up to a total volume of 500 μl) was assayed for enzymatic activity by incubation with 1 μCi [1]$^3$H-GGPP for 1 hour in 20 mM Tris buffer (pH 7.7, 3 mM EDTA, 5 mM β-mercaptoethanol, 5 mM MgCl$_2$). Samples were quenched, extracted with 500 μl hexanes and partially purified by passing through a small silica gel pasteur pipette column. Elisabethatriene was then added as "cold carrier" and incubations were purified by high-performance liquid chromatography (HPLC). During the HPLC analyses, fractions were collected before and after the elisabethatriene peak to demonstrate radiochemical purity and prove that the radioactivity obtained from the silica gel column was due to elisabethatriene. Radioactivity in HPLC fractions was quantified by scintillation counting.

As one example of a purification protocol used to purify the cyclase, a CFE sample was prepared using 140 g of flash frozen *P. elisabethae* and 200 mL of buffer A [20 mM Tris buffer (pH 7.7, 3 mM EDTA, 5 mM β-mercaptoethanol, 5 mM MgCl$_2$)]. This CFE was loaded onto a DEAE ion-exchange column and eluted with a step gradient of increasing NaCl from 0 to 10 mM in 5 mM increments using buffer B [20 mM Tris buffer +1 M NaCl (pH 7.7, 3 mM EDTA, 5 mM β-mercaptoethanol, 5 mM MgCl$_2$)]. The active fractions, which eluted at 10 mM NaCl, were concentrated, exchanged by ultracentrifugation into buffer C [buffer A +1 M (NH$_4$)$_2$SO$_4$ (pH 7.7, 3 mM EDTA, 5 mM β-mercaptoethanol, 5 mM MgCl$_2$)], and subjected to chromatography on a phenyl sepharose CL-4B column. Proteins were eluted with a decreasing salt gradient from 15 to 0 mM (NH$_4$)$_2$SO$_4$ in 5 mM increments by increasing the percentage of buffer A. Most of the elisabethatriene cyclase activity eluted from the column with 0 mM (NH$_4$)$_2$SO4. The fractions obtained were concentrated, exchanged into buffer D[1 mM potassium phosphate buffer (pH 6.0, 5 mM β-mercaptoethanol, 5 mM MgCl$_2$)], and loaded onto a Bio-scale ceramic hydroxyapatite CHT5-I column. Fractions were eluted from the hydroxyapatite column with a linear gradient of increasing potassium phosphate concentration (35 to 110 mM) by increasing the percentage of buffer E[500 mM potassium phosphate buffer (pH 6.0, 5 mM β-mercaptoethanol, 5 mM MgCl$_2$)]. Elisabethatriene cyclase activity was observed when the gradient reached approximately 100 mM potassium phosphate. The final purification step included buffer exchange by ultracentrifugation into buffer A and separation of protein on an UNO™ Q1 continuous bed ion-exchange column. Protein was eluted using a linear gradient of increasing buffer B (40 to 140 mM NaCl) and the elisabethatriene activity eluted from the column between 50 and 80 mM NaCl.

Figure 2:
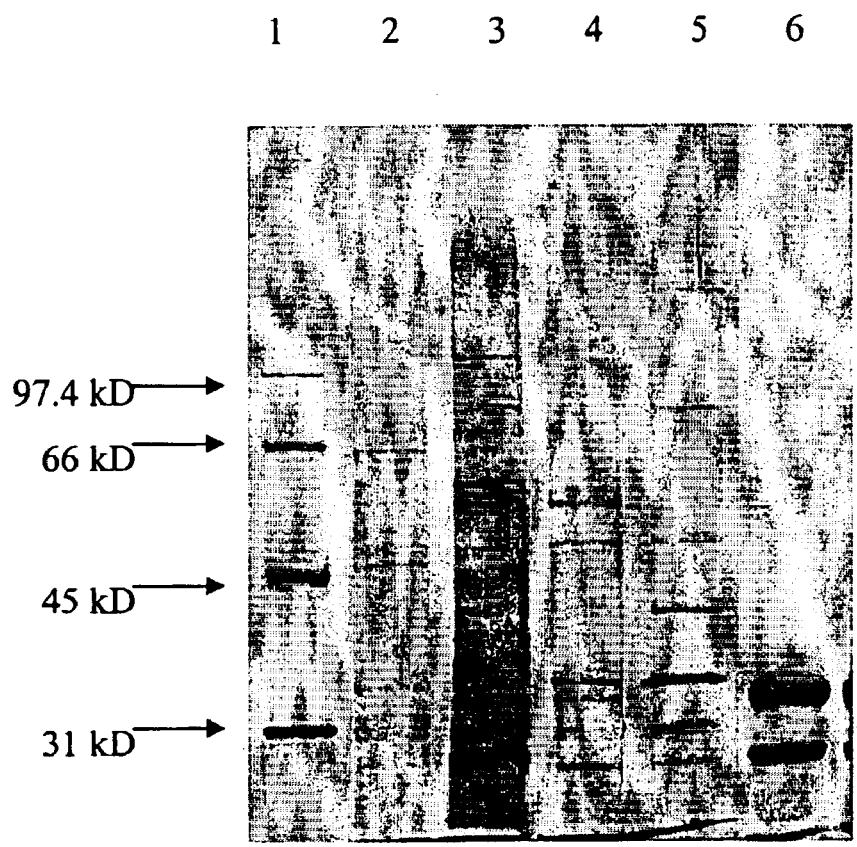

After these purification steps, the purity of each protein fraction was determined using SDS-PAGE electrophoresis (FIG. 2). The molecular weight of the elisabethatriene cyclase was confirmed to be about 47,000 daltons by comparison to calibration standards on a Sephadex G-100 superfine size exclusion column. In addition, the isoelectric point (pI) of elisabethatriene cyclase was determined to be 5.1 using an isoelectric focusing gel in which the bands were excised and assayed for enzymatic activity. For sequencing, the SDS-PAGE bands at about 47,000 daltons were excised from a 7.5% gel of active fractions from the UNO™ ion-exchange column. The excised bands were subjected to Edman degradation sequencing. The sequences of four of the resulting peptides sequences are shown in FIG. 4.

Example 2
Cyclizing GGPP to Elisabethatriene

Using elisabethatriene cyclase purified by column chromatography as described in Example 1, GGPP was cyclized to elisabethatriene. To carry out the reaction, incubations were performed by incubating $^3$H-GGPP(1 $\mu$Ci) with purified elisabethatriene cyclase-containing fractions from chromatography columns at 27° C. for 1–4 hours. Purified cyclase elisabethatriene preparations analyzed catalyzed the cyclization of GGPP to elisabethatriene. Adding protease inhibitors (e.g., pepstatin, leupeptin and chymostatin) in this process did not increase the enzymatic activity of the fractions as judged by the formation of pseudopterosins.

Example 3
Pseudopterosin Biosynthesis

Pseudopterosin biosynthesis was characterized by performing a detailed chemical analysis of specimens of *P. elisabethae* collected in diverse geographic locations. *P. elisabethae* were collected from three regions of the Bahamas and a recently discovered site in the Florida Keys. From very careful analyses of these samples, over 20 metabolites, many of which are potential intermediates in the pseudopterosin/seco-pseudopterosin biosynthetic pathway (e.g., compounds 18, 19, 20, 22, 24, 25, 27) were identified. Experiments were carried out to confirm the intermediacy of a number of these metabolites. These experiments suggested the pathway shown in FIG. 1 as the metabolic origin of this group of diterpenes.

Figure 3:
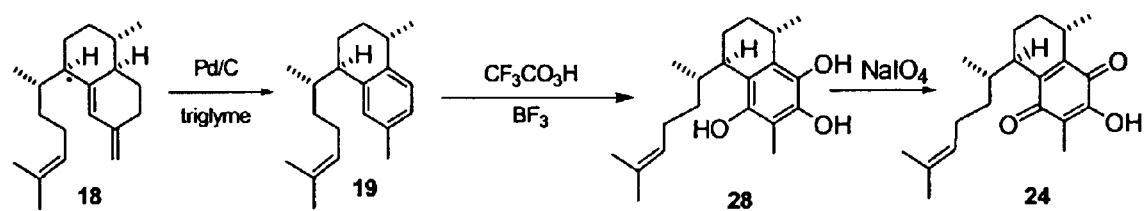

Using purified elisabethatriene cyclase coupled with other known chemical methods, various pseudopterosins can be made from a GGPP substrate. Referring to FIGS. 1 and 3, the first step of the chemical transformation of elisabethatriene to elisabethadione is the aromatization of compound 18. Aromatization of compound 18 was accomplished using Pd/C in refluxing trigylme for 3 hours (Garrett Tetrahedron Letters 3:191–194, 1969) which afforded compound 19 in a yield of ca. 50%. Alternatively, compound 19 can be generated using $H_5PMo_{10}V_2O_{40}(H_2O)_{32}$ in 1,2-dichloroethane at 70° C. under an $O_2$ atmosphere (R. Neuman et al., J. Org. Chem 54:4607–4610, 1989). The synthesis of compound 24 is completed by oxidation of compound 19 first with $CF_3CO_3H/BF_3$ and then $NaIO_4$ using standard methods (Ucciani et al., J. Baudet Bull. Soc. Chim. Fr. 871, 1962). Compound 19 is oxidized to compound 28 with dimethyldioxirane (DMD) in acidic medium. Bernini et al., Tetrahedron Lett. 41:1087–1090, 2000. Subsequently, oxidation of compound 28 is performed using Fremy's salt (potassium nitrosodisulfonate) (Matsumoto et al., Biorg. Med. Chem. Lett. 8:2945–2948, 1998) or nitrogen dioxide and oxygen (Bozell et al., Tetrahedron Lett. 39:2261–2264, 1998).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A purified protein isolatable from a coral sample comprising Pseudopterogorgia elisabethae, the purified protein having the following characteristics:

(A) an apparent molecular weight of about 47,000 Da;

(B) an isoelectric point of about 5.1; and (C) the ability to cyclize geranyl geranyl diphosphate, wherein the purified protein comprises the amino acid sequences of SEQ ID NO:1. SEQ ID NO:2. SEQ ID NO:3 and SEQ ID NO:4.

2. The protein of claim 1 purified from a coral sample comprising Pseudopterogorgia elisabethae by a method comprising the steps of:

(A) preparing a cell free extract from the sample;

(B) separating the cell free extract into at least one fraction that exhibits elisabethatriene cyclase activity and at least one fraction that does not exhibit elisabethatriene cyclase activity; and (C) collecting the at least one fraction that exhibits elisabethatriene cyclase activity.

3. The protein claim 2, wherein step (A) comprises:

flash freezing the sample using liquid nitrogen;

homogenizing the frozen sample with a buffer and liquid nitrogen;

separating the homogenized sample into a cellular portion and a non-cellular portion; and collecting the non-cellular portion.

4. The protein of claim 3, wherein step (B) comprises subjecting the cell free extract to at least one chromatographic separation step.

5. The protein of claim 4 wherein the chromatographic separation step comprises DEAE ion exchange chromatography.

6. The protein of claim 4 wherein the chromatographic separation step comprises phenyl sepharose chromatography.

7. The protein of claim 4, wherein the chromatographic separation step comprises hydroxyapatite chromatography.

8. The protein of claim 4, wherein the chromatographic separation step comprises ion exchange chromatography with 2-Propen-1-aminium, N,N,-dimethyl-N-2-propenyl-, chloride, polymer with 1,4-bis(1-oxo-2-propenyl)piperazine and 2-methyl-2-propenamide.

* * * * *